United States Patent [19]

Harris et al.

[11] 4,205,686
[45] Jun. 3, 1980

[54] ULTRASONIC TRANSDUCER AND EXAMINATION METHOD

[75] Inventors: Daniel J. Harris, West Hartford; Richard B. Bernardi, Cheshire, both of Conn.

[73] Assignee: Picker Corporation, Cleveland, Ohio

[21] Appl. No.: 831,779

[22] Filed: Sep. 9, 1977

[51] Int. Cl.² ............................................. A61B 10/00
[52] U.S. Cl. ..................................... 128/660; 73/644; 310/336
[58] Field of Search ............... 128/2 V, 2.05 Z, 24 A, 128/660–663; 73/632–633, 642, 644, 643; 310/328, 336–337, 367, 371

[56] References Cited

U.S. PATENT DOCUMENTS

| | | | |
|---|---|---|---|
| 2,430,013 | 11/1947 | Hansell | 128/24 A |
| 2,645,727 | 7/1953 | Willard | 310/371 |
| 3,277,451 | 10/1966 | Parssinen | 340/10 |
| 3,687,219 | 8/1972 | Langlois | 73/644 |
| 3,847,141 | 11/1974 | Hoop | 73/632 |
| 3,891,871 | 6/1975 | Henriquez et al. | 310/371 X |
| 3,938,502 | 2/1976 | Bom | 128/2 V |
| 3,958,559 | 5/1976 | Glenn et al. | 128/2 V |
| 3,971,962 | 7/1976 | Green | 73/641 X |

OTHER PUBLICATIONS

Steidel, K. D., "An Introduction to the Physics of Diagnostic UTS", Applied Radiology/UTS, Mar.–Apr., 1977, pp. 155–165.

*Primary Examiner*—Robert W. Michell
*Assistant Examiner*—Francis J. Jaworski
*Attorney, Agent, or Firm*—Watts, Hoffmann, Fisher & Heinke Co.

[57] ABSTRACT

An ultrasonic system and method for examining the structure of a subject body is disclosed. The system includes an improved ultrasonic transducer and power circuitry for electrically stimulating the transducer to produce an incident ultrasonic energy beam along a path extending into the subject. The incident beam produces echoes within the subject, some of which propagate back toward the transducer. The transducer, in response to received echoes, produces electrical signals bearing information about the structure of the subject. The system further includes circuitry for processing the electrical signals and a display apparatus responsive to the processed electrical signals for producing a visual display of subject structure.

The transducer includes a concavo-convex piezoelectric emitter for producing ultrasonic energy having a dominant frequency, an acoustical impedance matching transformer and a coupling element. The impedance matching transformer includes a concavo-convex portion of material having a radius of curvature similar to that of the emitter, and being nested in contact with the emitter. The transformer has a uniform thickness equal to one-fourth of the wave length of the dominant ultrasonic frequency within the transformer. The characteristic acoustic impedance of the transformer material is approximately the geometric mean of the characteristic acoustic impedance of the emitter and the subject. The coupling element is made of material having acoustic characteristics similar to that of the subject body and is acoustically couplable between the impedance matching transformer and the subject surface, having a generally flat surface for contacting the subject.

9 Claims, 3 Drawing Figures

ULTRASONIC TRANSDUCER AND EXAMINATION METHOD

BACKGROUND OF THE INVENTION

1. Field of the Invention

This invention relates to apparatus and method for examination of a subject, such as a human body, by deriving a display representing subject structure from electrical signals produced by ultrasonic echoes within the subject which occur in response to the direction of an ultrasonic energy beam into the subject.

2. Description of the Prior Art

Systems are known for examining the internal structure of a subject, such as an animal body, by directing an incident ultrasonic energy beam into the subject, detecting effects of the beam within the subject, and producing from the detected effects a visual display indicating characteristics of the internal subject structure.

Such systems have included an ultrasonic transducer, and power circuitry for actuating the transducer to propagate an incident ultrasonic beam. Ultrasonic echoes occur within a subject when incident beam waves are propagated across interfaces within the subject. These interfaces are between tissue structures having differing acoustical characteristics, such as differences in density and acoustic velocity. The transducer included means responsive to the receipt of energy from these echoes to produce representative electrical signals. Some of the echo energy propagated back toward, and was detected by, the transducer.

Such systems further included display apparatus, and processing circuitry responsive to the electrical signals from the transducer to generate a visual image representing internal subject structure.

Prior art transducers have included an emitter element made of a piezoelectric substance which was responsive to the application of electrical voltage pulses to produce the incident ultrasonic beam. Conversely, the piezoelectric element was responsive to the receipt of ultrasonic echo energy to produce the electrical signals representing characteristics of the echoes.

Ultrasonic transducers have also typically included elements for coupling the transducer acoustically with the surface of the subject, to facilitate transmission of ultrasonic energy between the emitter and the subject. Such coupling elements have included a flat output surface for effectively establishing a uniform contact between the transducer and the subject surface. Coupling elements have sometimes been disposed to contact the emitter intimately, for optimum energy transfer to and from the emitter.

Transducer emitters having a flat disc-shaped configuration have been employed. The incident energy produced by the respective portions of a flat emitter proceed, unfocused, outwardly from the emitter along generally parallel paths.

An unfocused beam is normally inferior to a focused beam. It is often desirable to concentrate the incident energy on a particular portion of the subject, an operation that can most readily be accomplished if the ultrasonic incident energy is focused at a predetermined distance from the transducer.

To correct for this lack of emitter beam focus, it has been proposed to provide emitters having concavo-convex configuration, with the energy emitting face being concave. The ultrasonic energy emanating from the various portions of the concave emitter face converge toward a predetermined region located generally at a predetermined focal distance from the emitter. The focal distance of such an emitter is a function of the radius of curvature of the emitting surface.

Ultrasonic transducers have also included transformer elements for improving matching between differing characteristic acoustical impedances of the emitter and the subject. Improvement of this acoustical impedance matching enhances the efficiency of acoustical energy transfer to and from the subject by reducing energy losses due to acoustical reflections occurring when acoustical energy passes across interfaces between the emitter and the subject. Good impedance matching also reduces undesirable acoustical reverberations, or "ringing," within components of the transducer.

Every substance, or "medium" has a "characteristic acoustical impedance". The characteristic acoustical impedance of a medium is a function of the product of its density and the velocity at which acoustical waves propagate within the medium. For biological tissue, the acoustic velocity is substantially constant for each medium, regardless of acoustic frequency. Piezoelectric emitters generally have acoustical impedances of from 15 to 20 times greater than that of biological tissue, such as human body tissue.

When acoustical energy crosses an interface between two media having different acoustical impedances, echoes are reflected back from the interface. These echoes embody a depletion, or loss, of part of the energy of the incident acoustical wave. The greater the echo at an interface, the greater is the fraction of incident acoustical energy which is depleted from the wave which penetrates into the subsequent medium.

The occurrence of these echoes within the transducer structure itself is undesirable because it introduces spurious ultrasonic energy waves within the transducer. These spurious ultrasonic waves are translated by the transducer emitter into spurious electrical signals which interfere with desirable information bearing echoes representing signals from within the subject, and ultimately detract from the quality of the image derived from the processed electrical signals.

Acoustical impedance transformer elements have been used in association both with transducers having flat emitting surfaces, and with those having concave emitter surfaces for focusing the ultrasonic beam. The use of curved impedance transformers has been proposed for application to transducers with concave emitter surfaces.

When a flat impedance transformer was disposed across a concave transducer emitting face, excessive echoes and reverberations were generated within the transducer structure itself. These reverberations resulted from the fact that, in such a combination of emitter and transformer, there necessarily was a variation in thickness between the facing surfaces of the transformer and emitter. Because the thickness was not quarter wave matched over the entire surface unwanted echoes were generated. These echoes were undesirable because they caused the transducers to produce spurious electrical signals, interfering with signals generated from echoes emanating from within the subject.

To eliminate the problem of the void between the emitting face and the impedance transformer, it was proposed to provide an impedance transformer having a curved surface suitable for intimate contact with the curved emitting face, and a flat side opposite the emitting face for contacting the subject efficiently. A disadvantage of this transformer was that it was not uniform in thickness. It therefore did not, by definition, have uniform impedance matching characteristics as to all the acoustical energy of a given dominant frequency emanating from the emitting surface. The flat face of the transformer could not practicably be altered, (to give uniformity of thickness) because its planar character was necessary for efficient mechanical contact with the subject surface.

It has been proposed to employ a "quarter wave acoustical impedance transformer" element in the path of the ultrasonic beam generated by the emitter to effect a better impedance match between the emitter and the subject. A quarter wave acoustical impedance transformer has been embodied by a flat disc of material having a uniform thickness chosen to be approximately one-fourth of the wave length within the transformer of the dominant frequency of acoustical energy produced by the emitter. It is known that the interposition of a quarter wave transformer between a source of acoustical energy and a subject, or "load," receiving the acoustical energy, changes the effective acoustical impedance as seen by the source. More specifically, the interposition of the quarter wave transformer presents an acoustical impedance to the source which is a function of the square of the characteristic acoustical impedance of the transformer material divided by the characteristic acoustical impedance of the load. Therefore, a quarter wave transformer can be used to modify the terminating or "load" impedance as seen by the source. Proper choice of transformer thickness and material can thus be used to modify load impedance seen by the emitter to more closely "match" that of the emitter itself. The improved matching, as noted, reduces reverberations and facilitates energy material transfer to the subject.

Transformers having thicknesses of non-unity odd quarter wave length multiples have also been found useful in impedance matching.

Techniques and theory of acoustical impedance matching are explained in the following article, expressly incorporated by reference: Kossoff, G., Vol SU-13, *IEEE Transactions on Sonics and Ultrasonics*, pp. 20–30.

SUMMARY OF THE INVENTION

It is a general purpose of this invention to provide an improved focused ultrasonic transducer and method which enables desired quarter wave acoustic impedance transformation, while at the same time providing for a desirable flat surface for optimum mechanical contact between the transducer and the subject for efficient acoustical energy transfer between the subject and the transducer.

The apparatus and method of this invention overcomes the difficulties and disadvantages of the prior art by providing an ultrasonic system having a transducer which effectively matches subject and emitter impedances, while at the same time providing a desirable flat output transducer surface, for facilitating ultrasonic energy transfer between the transducer and the subject.

A system embodying the present invention includes a transducer, power circuitry for actuating the transducer to direct an incident ultrasonic beam into a subject, to generate echoes, circuitry for processing electrical signals produced by the transducer in response to received ultrasonic echoes, and a display responsive to the processed electrical signals to derive a visual image representing internal subject structure.

According to one aspect of the invention, the transducer includes a housing, a concavo-convex emitter having a concave emitter surface for producing acoustical energy having a dominant frequency, and damping material adjacent the convex emitter face for reducing reverberations. The transducer also includes impedance transforming structure including a portion of material having a concavo-convex curvature substantially matching that of the emitter, and being nested adjacent the concave emitter face in intimate contact therewith. The transformer has a thickness which is chosen to be approximately one-fourth of a wave length of acoustical energy of the dominant frequency within the transformer.

According to another feature, the transducer also includes coupling structure including a portion of material having acoustical characteristics similar to those of the tissue of the examined subject. The coupling structure has a convex surface positioned in intimate contact with the concave surface of the impedance transformer, and a generally flat output face for effective mechanical contact with the subject surface.

This transducer assembly allows for the provision of an impedance transformer having a uniform quarter wave thickness, and has additionally a generally flat output surface which is desirable for effective contact with the subject, enabling improved performance of the ultrasonic system.

According to another aspect of the invention, the quarter wave transformer is made of a material whose characteristic acoustic impedance is approximately equal to the geometric mean of the characteristic acoustic impedances of the emitter and the subject being examined.

Another feature of the invention is that the coupling structure is made of a substance having a density and an acoustical velocity whose product is similar in magnitude to that of animal body tissue. The choice of such material enables the coupling structure and the subject body tissue to be considered as substantially indistinguishable for acoustical purposes, and reduces echoes and reverberations emanating from the subject surface (such as the skin line) which would interfere with signals derived from echoes occurring within the subject.

According to a still more specific aspect of the invention, one example of such coupling material is an elastomeric polyurethane.

Another aspect of the invention includes a method of examining a subject by the use of acoustical energy produced by a focusing emitter including the steps of stimulating the emitter to produce the acoustical energy, passing the acoustical energy from a substantial expanse of the emitter through a quarter wave impedance transformer and transmitting the acoustical energy into the subject by way of a portion of tissue equivalent material.

Another feature of the invention includes an acoustical transducer for an ultrasonic system having a focusing emitter and two layers of solid material positioned along the energy path from the emitter. One of the two layers comprises an acoustical impedance transformer, and the other constitutes a coupling layer including a portion of solid material having acoustical characteristics similar to those of the subject body.

A further aspect includes an ultrasonic transducer assembly having an emitter and a portion of solid material interposed in the path of the acoustical energy produced by the emitter, the solid material having acoustical characteristics similar to those of the examined subject.

A further feature includes a transducer having a focused emitter with a concave emitting face and a concavo-convex impedance transformer of uniform thickness adjacent the concave emitter face.

A broader feature is that the acoustic impedance transformer has a thickness of a non-unity odd quarter wave multiple of the acoustic wave length of the dominant frequency within the transformer.

The present invention will be better understood by study of the appended detailed description and claims, with reference to the included drawings, in which:

DESCRIPTION OF THE PREFERRED EMBODIMENT

Figure 1:
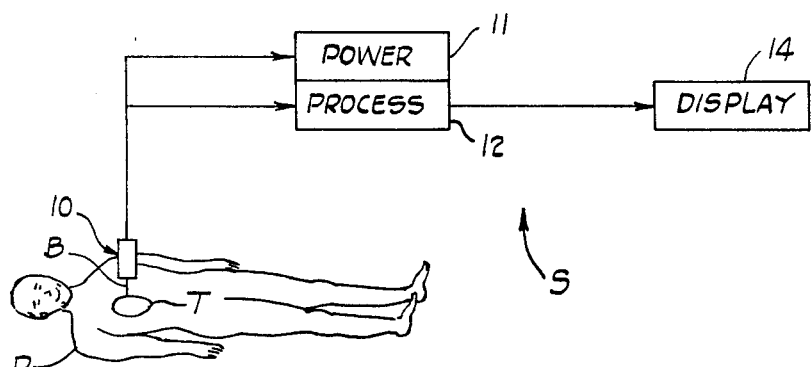
FIG. 1 is a simplified block diagram illustrating a system incorporating the invention.

An ultrasonic system S incorporating the present invention is illustrated in block form in FIG. 1. The system S produces an image of internal structure of a subject by the use of ultrasonic energy directed into the subject.

The system S includes a transducer 10, power and processing circuitry 11, 12, and a display apparatus 14. The transducer 10 is actuated by the power circuitry 11 to direct an ultrasonic beam B into a subject, such as a patient P. When the beam B strikes an interface with a tissue mass such as T within the patient P, ultrasonic echoes are produced, some of which propagate back toward the transducer 10. The transducer 10, in response to received echoes, produces electrical signals bearing information relating to the characteristics of the echoes representing the structure of the tissue mass T, and directs these electrical signals to the processing circuitry 12. The processing circuitry 12, in response to the electrical signals, actuates the display apparatus 14 to produce a visual image representing internal structure of the patient P, such as the configuration of the tissue mass T.

Figure 2:
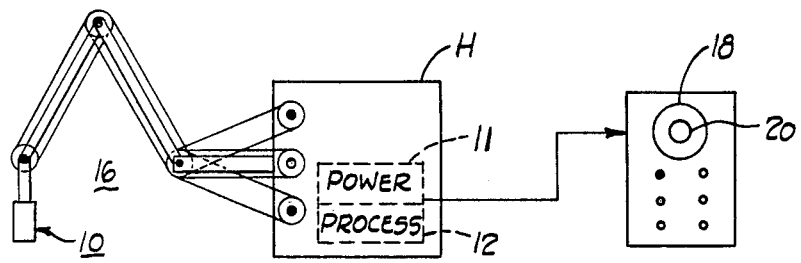
FIG. 2 is an elevational drawing illustrating the system shown in FIG. 1.

The system S is illustrated in somewhat more detail in FIG. 2. FIG. 2 illustrates a housing structure H which includes the power and processing circuitry 11, 12 therein. Also illustrated is an articulated arm structure 16 connecting the transducer 10 with the housing H. The articulated arm structure 16 also includes electrical connections (not shown) between the transducer 10 and the power and processing circuitry 11, 12 to enable the power circuitry to actuate the transducer 10, and to provide a transmission path for electrical signals representing sensed echoes from the transducer to the processing circuitry 12.

The processing circuitry 12 is connected to the display apparatus 14. The display apparatus 14 is suitably embodied by a cathode ray tube oscilloscope having a screen 18 upon which an image 20 representing internal subject structure is displayed in response to electrical signals processed by the circuitry 12.

The articulated arm structure 16, the housing H, its enclosed power and processing circuitry 11, 12 and the display apparatus 14 are suitably embodied by apparatus and circuitry disclosed in U.S. Pat. No. 3,924,452, issued Dec. 9, 1975 to Edward P. Meyer, et al, entitled "Sector Scanning Ultrasonic Inspection Apparatus," which patent is expressly incorporated by reference here. The structure and circuitry described in the referenced patent is in turn embodied by an ultrasonic system Model 80L manufactured and sold by Picker Corporation, of Northford, Conn., U.S.A.

Figure 3:
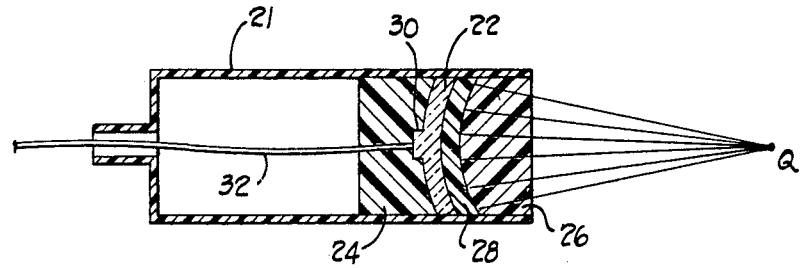
FIG. 3 is a detailed elevational view, in cross section, illustrating a portion of the system of FIGS. 1 and 2.

The transducer 10 is illustrated in detailed form, partially broken away, in FIG. 3. The transducer 10 includes a transducer housing 21 and an emitter element 22 disposed within the housing. A portion of damping material 24 is also disposed within the housing adjacent one side of the emitter element 22. A coupling element 26 is fixed within the housing 21 on the opposite side of the emitter 22 from the damping material 24. Interposed between the emitter 22 and the coupling element 26 is an acoustical impedance transformer element 28. Electrically conductive structure, including an electrode 30 and an electrical lead 32 is electrically connected to the side of the emitter 22 adjacent the damping material 24. The electrically conductive structure facilitates the application of an electrical voltage to the emitter 22 for stimulating the emitter to produce an ultrasonic energy beam emanating outwardly from the transducer through the impedance transformer 28 and the coupling element 26.

The transducer housing 21 suitably comprises a generally cylindrical insulative structure having relatively thin walls for accommodating therein other components of the transducer 10. Typically, the transducer housing 21 is made of a nylon material called "Delrin," and is approximately three inches in length, with a diameter of about one inch.

The emitter 22 is a concavo-convex portion of piezoelectric material having convex and concave faces. The concave emitter face serves as the emitting surface of the emitter 22. The emitter 22, when electrically stimulated by the application of an electrical voltage to its electrode 30, produces a substantially focused ultrasonic energy beam. The curvature of the convex face of the emitter 22 preferably has a radius selected such that the ultrasonic energy produced by the respective portions of the concave emitter face converge to focal point Q aligned with the emitter and located ideally at an axial displacement of between 5 and 10 centimeters from the concave emitter face.

The emitter element 22 is preferably made in a circular concavo-convex configuration, and a diameter approximately equal to the inside diameter of the housing 21. The emitter 22 is fixed to the inside of the housing 21 by means of a suitable adhesive substance. Typically, the emitter 22 is fabricated from a portion of lead zirconate titanate, which is sometimes referred to as "PZT," which has a characteristic acoustic impedance of about $25 \times 10^5$ to $30 \times 10^5$ Rayls.

The electrode 30 is preferably made of silver adhered in electrical contact to the convex face of the emitter 22. The lead 32 is a length of suitably conductive wire, such as copper, gold or silver.

An electrical pulse with a broad frequency distribution impressed upon the lead 32 will stimulate the emitter 22 to produce ultrasonic waves having a dominant frequency of generally between 1 megahertz (MHz.) and 10 MHz.

The damping element 24 is preferably a portion of epoxy material filled into the housing adjacent the convex face of the emitter 22 and in intimate contact therewith, over the area of the convex emitter face which is not covered by the electrode 30. Preferably, the damping element 24 is approximately $\frac{1}{4}''$ to $\frac{1}{2}''$ in length.

The acoustic impedance transformer 28 is a quarter wave transformer and consists of a portion of epoxy material formed in a concavo-convex configuration having a radius of curvature substantially equal to that of the emitter 22. The transformer 28 is aligned with its convex face nested in intimate contact adjacent the concave emitter face. The transformer element 28 has a uniform thickness which is calculated to be approximately one-fourth of the wave length, within the transformer, of the acoustic waves of the dominant frequency produced by the emitter 22. Since the emitter 22, in practice, does not produce only a single discrete frequency of acoustic waves, but rather a distribution of acoustic frequencies about a dominant frequency, the thickness of the transformer element 28 is chosen to be one-fourth of the wave length of acoustic waves of the dominant frequency.

Preferably, the emitter 22 is actuated in known fashion by a train of electrical voltage pulses, each of a broad frequency spectrum, impressed upon its electrode 30 by way of the conductor 32. For example, the acoustic waves produced by the emitter 22 may have a dominant frequency of approximately 2 MHz., and, in a preferable epoxy material chosen, a wave length of approximately 1 millimeter (mm), dictating that the thickness of the impedance transformer 28 be chosen as approximately 0.25 millimeters.

It has been found that the transformer can also suitably have a thickness of a any odd quarter wave multiple. In the preferred example, the thickness could be 0.75 mm., 1.25 mm., 1.75 mm., and so on.

It is preferably that the characteristic acoustic impedance of the material of the transformer 28 be approximately equal to the geometric mean of the characteristic acoustic impedances of the emitter material and the subject. If the emitter material is regarded as having an impedance of $30 \times 10^5$ Rayls, and human subject body tissue is considered to have an impedance of about $1.5 \times 10^5$ Rayls, the preferred transformer characteristic impedance is about $6.7 \times 10^5$ Rayls.

The coupling element 26 is formed to have a convex surface in intimate contact with the concave surface of the transformer 28. The surface of the coupling element 26 opposite the transformer 28 is preferably planar, for optimum mechanical contact with most of the surfaces of the subject, such as a human body, being examined.

Preferably, the coupling element 26 is made of a portion of homogeneous elastomeric polyurethane material. The polyurethane material is chosen to have acoustical characteristics similar to those of the human body tissue. Specifically, the most suitable material known at this time for the coupling element 26 is an elastomeric polyurethane material manufactured to have a density of approximately 1.2 grams per cubic centimeter and an acoustic velocity of approximately 1250 meters/second.

In operation, (utilizing the preferred embodiment) the electrical voltage impulses are applied to the emitter 22 by way of the electrode 30 and the conductive lead 32. The emitter 22 produces ultrasonic waves of a dominant frequency of about 2 megahertz emanating from its concave surface and passing through the transformer 28 and the coupling element 26. The quarter wave transformer 28 modifies the acoustic impedance seen by the emitting concave face of the emitter 22 to a value of approximately $30 \times 10^5$ Rayls. This is derived from the above noted fact that the impedance seen by the emitter is the square of the transformer characteristic impedance, divided by the "load" impedance. The acoustic impedance of the emitter material being approximately the same, this modified impedance seen by the emitter 22 matches the characteristic acoustic impedance of the emitter material itself.

It is thus seen that the transducer 10 of this invention provides for improved efficiency of acoustical energy transfer into the subject body, and reduces the magnitude of reverberations or "ringing" within the various elements of the transducer, by means of an improved impedance match between the emitter 22 and the subject body. At the same time the coupling element provides a mechanically efficient flat surface for contact between subject and transducer.

The description of the present invention is intended to be illustrative, rather than exhaustive, and it is to be recognized that persons of ordinary skill may make certain modifications, changes or additions to the specific structure and method described, without departing from the spirit of the invention, or its scope, as expressed in the appended claims.

What is claimed is:

1. An ultrasonic transducer assembly for an ultrasonic system for examining an animal body by propagating ultrasonic energy through the body, said assembly comprising:
   (a) housing structure;
   (b) an emitter including a concavo-convex portion of piezoelectric material having concave and convex faces and being disposed within the housing structure for emitting acoustical energy having a frequency distribution about a dominant frequency in response to electrical stimulation of the emitter;
   (c) damping material adjacent the convex emitter face;
   (d) an impedance transformer including a portion of material having a concavo-convex curvature substantially matching that of said emitter and being nested adjacent the concave emitter face, said portion having a substantially uniform thickness of approximately one-fourth of a wave length of acoustical energy of said dominant frequency propagating through the portion, and
   (e) coupling structure including a portion of solid tissue equivalent material having acoustical characteristics similar to those of the tissue of the examined animal body, said coupling structure having a convex face disposed adjacent the concave side of the impedance transformer opposite the emitter and having a generally flat face opposite its said convex face for efficiently contacting substantially flat portions of the animal body.

2. The ultrasonic transducer assembly of claim 1, wherein said coupling structure has a characteristic acoustical impedance similar to that of tissue of the subject animal body.

3. The ultrasonic transducer assembly of claim 1, wherein said coupling structure is made of elastomeric polyurethane.

4. The ultrasonic transducer assembly of claim 1, wherein said impedance transformer is constructed of an epoxy material.

5. The ultrasonic transducer assembly of claim 1, wherein said emitter comprises a portion of lead zirconate titanate ceramic material.

6. The ultrasonic transducer assembly of claim 1, further comprising:

electrically conductive structure connected to said emitter for facilitating its electrical stimulation.

7. An ultrasonic system for examining structure of a subject, said system comprising:

(a) a display apparatus for producing a visual image representing such structure;

(b) processing circuitry responsive to electrical signals for actuating the display apparatus;

(c) power actuation circuitry;

(d) an ultrasonic transducer comprising:

(i) housing structure;

(ii) a focusing emitter having a concavo-convex configuration responsive to actuation from the power actuation circuitry for producing ultrasonic energy having a dominant frequency;

(iii) damping material adjacent a convex face of the emitter;

(iv) an impedance transformer including a portion of material having a concavo-convex curvature similar to that of said emitter and nested adjacent a concave emitter face, said portion of material having a substantially uniform thickness over a substantial area of said material of approximately one-quarter of a wave length of acoustical energy of the dominant frequency within the transformer, and (v) said emitter having a first characteristic acoustic impedance, and said transformer having a characteristic acoustic impedance of approximately the geometric mean of said first characteristic impedance and characteristic acoustic impedance of the subject, and (vi) a portion of solid material having acoustical characteristics similar to that of the subject being examined, said solid material having convex face nested substantially adjacent the concave face of the impedance transformer and a substantially flat face opposite the convex face for facilitating acoustical contact with a substantially flat portion of the subject being examined.

8. An acoustical energy transducer assembly for examining a subject, the transducer assembly comprising:

(a) a curved concavo-convex emitter having a characteristic acoustic impedance and being responsive to the application of electrical energy thereto to emit substantially focused acoustical energy having a dominant frequency;

(b) a concavo-convex acoustical impedance transformer disposed in a path of said acoustical energy, said acoustical impedance transformer having a uniform thickness substantially equal to an odd multiple of one-quarter of the wave length within the transformer of acoustical energy of the dominant frequency, said acoustical impedance transformer being disposed with its convex face substantially adjacent the concave face of the emitter, and (c) a plano-convex portion of solid material having acoustical velocity and impedance approximately equal to that of animal tissue having a high water content, said portion being positioned with its convex face substantially adjacent the concave face of the transformer element.

9. The acoustical energy transducer assembly of claim 8, wherein:

said transformer is made of a material whose characteristic acoustic impedance is approximately the geometric mean of the characteristic acoustic impedances of the emitter and the subject.

* * * * *